United States Patent [19]

deJong et al.

[11] Patent Number: 4,981,362
[45] Date of Patent: Jan. 1, 1991

[54] PARTICLE CONCENTRATION MEASURING METHOD AND DEVICE

[75] Inventors: Joannes N. M. deJong, Suffern; Gerald A. Domoto, Briarcliff Manor; John J. Ricciardelli, Poughkeepsie; Gerhard H. Bay, Yonkers; Johann H. Metternich, North Tarrytown, all of N.Y.

[73] Assignee: Xerox Corporation, Stamford, Conn.

[21] Appl. No.: 422,319

[22] Filed: Oct. 16, 1989

[51] Int. Cl.$^5$ ............... G01N 21/00; G01N 15/06; G01J 1/32
[52] U.S. Cl. .................... 356/436; 356/442; 250/205; 250/575
[58] Field of Search ............ 356/433, 356, 435–442; 250/575, 574, 205

[56] References Cited

U.S. PATENT DOCUMENTS

| | | | |
|---|---|---|---|
| 3,652,850 | 3/1972 | Briggs | 250/43.5 R |
| 3,740,156 | 6/1973 | Heigl et al. | 356/433 |
| 3,976,891 | 8/1976 | Parkinson | 250/575 |
| 4,017,193 | 4/1977 | Loiterman | 356/206 |
| 4,037,973 | 7/1977 | Carr | 356/206 |
| 4,290,695 | 9/1981 | Schmitt | 356/442 |
| 4,433,585 | 2/1984 | Levine | 356/356 |

Primary Examiner—Richard A. Rosenberger
Assistant Examiner—Hoa Pham
Attorney, Agent, or Firm—Robert A. Chittum

[57] ABSTRACT

The method and apparatus for measuring the particle concentration in a fluid that is passed between a reciprocally movable window and a single photodetector. A collimated beam of light is directed through the window and fluid to the photodetector. The window is moved from a first predetermined location to a second predetermined location to vary the light beam path length, thus enabling at least two different photodetector output signals. The ratio of the two signals provides the data needed to determine the particle concentration in the fluid.

5 Claims, 4 Drawing Sheets

PARTICLE CONCENTRATION MEASURING METHOD AND DEVICE

BACKGROUND OF THE INVENTION

1. Field of the Invention

This invention relates to the measurement of the transmission of light through a medium, which can be either a gas, liquid, or solid, to determine the absorption coefficient thereof, and more particularly to the method and apparatus for determining the particle concentration in a fluid by use of a single photodetector to detect collimated light beams passed through the fluid along a variable light absorption path length.

2. Description of the Prior Art

It is known that the presence of dissolved substances in a liquid gives rise to the attenuation of a beam of light passing through the liquid and that the attenuation occurs selectively at differing wavelengths which are characteristic of different solutes. Hence, by measuring the attenuation of the light, that is, the optical density of the liquid at specific wavelengths, the concentration of the solutes can be measured, thus providing a method of analyzing the liquid. However, suspended solid matter also gives rise to the attenuation of the light passing through the liquid, but in this case, the attenuation occurs generally over most of the optical spectrum due to the absorption, scattering, or reflection of incident light by the particles of the suspended solids. Therefore, there will be an error introduced in the apparent concentrations of the solutes, by the overall attenuation due to the solid matter suspended in the liquid.

In another prior art example, the particulate content of stack emissions for power plants and similar installations must be limited to acceptable levels. This requires continuous monitoring and frequent checking of the performance of the monitoring apparatus.

Measuring optical transmittance of the smoke, etc. is one of the means available to evaluate the amount of particulate matter being discharged to the atmosphere. Since the amount will depend on the dimensions of the smoke stack, etc. as well as on the density of the particles in the gas, in general it is desired to determine that transmittance over a predetermined distance such as the stack diameter so that appropriate standards can be established and compliance therewith can be determined.

To determine light transmittance, it is necessary to transmit light through the gaseous medium and measure variations in attenuation produced by the particles therein. Variations in the intensity of the light source and in the sensitivity of the light sensor will commonly affect the measurement. Also, accumulation of dirt on optical windows through which the light passes will affect the measurement. In addition, scattering of the transmitted light by smoke particles and the like in the gaseous medium may affect the measuring accuracy.

U.S. Pat. No. 3,976,891 to Parkinson discloses a device for measuring the density of smoke which compensates for the accumulation of smoke particles, soot, or dust particles on the faces of windows which are exposed to the air or gas in which the particles to be detected are contained. Two separate windows are provided through which two separate beams of light are passed. The windows are spaced such that the respective beams passing through the windows pass different distances through the smoke. Photoelectric devices receive the light transmitted through the windows, and a bridge circuit compares the respective responses of the photoelectric means to determine the density of the smoke particles.

U.S. Pat. No. 4,017,193 to Loiterman discloses a device to measure the transmittance of a gaseous medium carrying particulate matter which is substantially unaffected by variations in light source brightness, dirt build up on optical windows, scattered light and photosensor sensitivity. First and second light sources and first and second light sensors are positioned opposite to each other. The sources and sensors are positioned to provide equal shorter path lengths between the first source and the first sensor and between the second source and the second sensor, and equal longer path lengths between the first source and the second sensor and between the second source and the first sensor. Each light source produces a narrow collimated beam directed toward each respective light sensor. Output signals of the sensors are fed to computing means which produces a quotient of the products of the output corresponding to light transmitted over the longer and shorter paths in order to measure the density of the smoke.

U.S. Pat. No. 4,037,973 to Carr discloses a sensing unit for suspended solids measurements having a single light source, a pair of photodetectors disposed on a common light path at different distances with respect to the light source, and a measuring circuit operatively connected thereto. The liquid with the suspended solids to be measured is disposed between the light source and the photodetectors, which are supported in fixed relationship with each other. A tubular opaque shield contains the light source and detectors and the ends provide ingress and egress of the liquid.

U.S. Pat. No. 3,652,850 to Briggs discloses method and apparatus for measuring the optical density of a fluid for light having wavelengths in a specific region of the electromagnetic spectrum. A first and second detecting means are provided for receiving light that has traveled through a sample of fluid over both longer and shorter light paths. A means for alternately directing the light through the fluid to associated detecting means so that each detecting means alternately receive light which has traveled along longer and shorter paths. The detectors provide a first signal related to attenuation of light and a second signal related to the concentration of solid matter in the fluid. The second signal is used by monitoring apparatus to correct the first signal for attenuation of the light by the suspended solid matter and thereby to provide an output signal indicative of the density of the fluid.

Particle concentration measuring devices exemplified above generally consist of a light source and a light intensity detector such as a photodiode with a fluid specimen placed between them. In such systems, various sources of errors exist which require expensive compensation techniques; viz., light source intensity variations, stray ambient light and photodiode dark current, detector sensitivity variations, and variations in optical component transmissibility. For example, compensation for light source intensity variations may be accomplished by deflecting part of the outgoing light sources beam with a beam splitter and measuring the intensity of this deflected beam, and compensation for stray light ambient light and photodiode dark current may be accomplished by modulation of the light intensity and use of a lock-in amplifier.

By use of the method and apparatus of the present invention with its unique feature of the use of a variable light absorption path length to measure absorption coefficients, the above errors of the prior art devices are removed.

SUMMARY OF THE INVENTION

It is an object of the present invention to provide a simple, compact, cost effective method and device to measure the light absorption coefficient and, therefore, the particle concentration in a fluid, gas or liquid, which compensates for light source intensity variations, detector sensitivity variations, and changes in transmissibility of optical components.

In the present invention, a method and apparatus are delineated in which the fluid with a particle concentration is passed between a single fixed photodetector or photodiode and a reciprocably movable window. A collimated beam of light is directed through the window and fluid to the photodetector. The window is translated along the optical path of the light beam i.e., towards and away from the photodetector, from a first predetermined location to a second predetermined location to vary the light absorption path length. This produces at least two different photodetector output signals which provides the data needed to determine the particle concentration in the fluid.

A more complete understanding of the present invention can be obtained by considering the following detailed description in conjunction with the accompanying drawings, wherein like parts have the same index numerals.

DESCRIPTION OF THE PREFERRED EMBODIMENT

Figure 1:
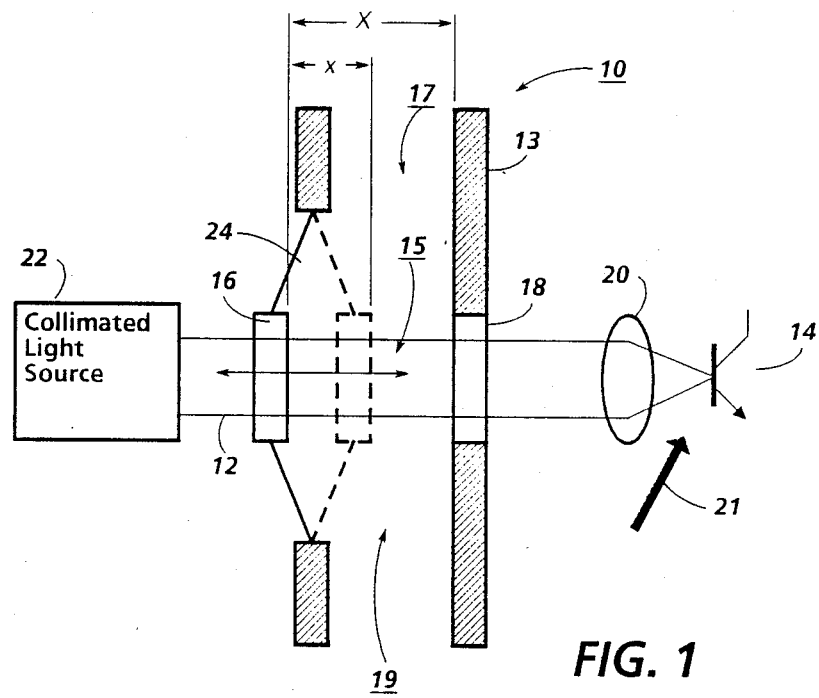
FIG. 1 is a schematic side elevation view of the operating principle of the particle concentration measuring device of the present invention.

The principle of operation of the particle concentration measuring device 10 of the present invention is shown in FIG. 1, schematically depicting the device in a side elevation view. A fluid (not shown), which may be either a gas or liquid containing a concentration of particles, is passed through a collimated light beam 12 and the transmittance is measured with a photodetector 14 such as a photodiode. A reciprocally movable window 16 varies the passageway or channel width 15 to produce a variable throat in the passageway through which the fluid flows from the maximum width "X" to minimum width "X-x", where x is the stroke of the window along the light beam path. The fluid channel 13 has entrance 17 and exit 19. The light source 22 emits a collimated light beam 12 which travels through the movable window 16, the fluid with a concentration of particles in the variable channel area 15, through the fixed channel window 18 and focusing lens 20, and into photodetector 14, which concurrently receives ambient light represented by arrow 21. The light source may be either a laser, light emitting diode (LED) or incandescent lamp. The flexible seal or diaphragm 24 enables leak-free movement of the movable window while narrowing the channel width. By varying the channel width, the current output or output signal of the photodetector or photodiode also changes. The ratio of the two measurements taken at two instances of time at two channel widths X and X-x provides the compensation for the errors produced by prior art devices and provides the following relationships:

$$I_X = (L_0 K_1 e^{-CX} K_2 + I_0) K_d \quad (1)$$

$$I_{X-x} = (L_0 K_1 e^{-C(X-x)} K_2 + I_0) K_d \quad (2)$$

where:
$I_X$—photodiode current at channel width X
$I_{X-x}$—photodiode current at channel width X-x
$L_0$—light source intensity
$K_1$—fixed window 1 transmissibility including dirt built up
$K_2$—movable window 2 transmissibility including dirt built up
X—nominal channel width
x—stroke of moving window
C—absorption coefficient per unit length at a particular wavelength (to be measured)
$K_d$—photodiode sensitivity
$I_0$—photodiode dark current and ambient light Computing the ratio R of the first two equations and assuming that the influence of $I_o$ can be neglected ($I_o = 0$, to be justified below), yields $$R = e^{-Cx} \quad (3)$$

Note that this absorption coefficient is a function of the wavelength. Here it is assumed constant over the spectrum of the source. This condition can be assured by (1) selecting a monochromatic light source, or (2) filtering to make the light monochromatic (filter in front of the detector or light source). Equation 3 also shows that the ratio R is not a function of light source intensity variations $L_o$, detector sensitivity variations $K_d$, and dirt built up on windows which affect transmissibility factors $K_1$ and $K_2$. Selection of appropriate photodiodes and circuit parameters should virtually eliminate the effect of dark current, whereas shielding minimizes ambient light. Should shielding be impossible, then the source intensity can be modulated and a lock-in amplifier be used to detect the signal. Equation 3 also shows that the R is independent of the nominal distance X; hence it can be adjusted to give sufficient light onto the photodiode. The length of the stroke can be adjusted to maximize sensitivity around a nominal density $C_o$ as illustrated below:

$$S = \frac{dR}{dC} = -xe^{-C_0 x} \quad (4)$$

where:
S—sensitivity of ratio R with respect to optical density C at $C = C_0$
$C_0$—nominal optical density This sensitivity is a function of the stroke x. Maximum sensitivity occurs when:

$$\frac{dS}{dx} = -e^{-C_0 x} + C_0 x e^{-C_0 x} = 0 \quad (5)$$

or:

$$C_0 x = 1 \quad (6)$$

Substituting this result in equation 1 gives $R = e^{-1}$. Hence, the maximum sensitivity to absorption coefficient variations around a nominal value $C_0$ is obtained when the stroke x is chosen so that the two photodiode currents at the two channel widths have a ratio of $e^{-1}$. This provides a convenient, practical method for selecting the optimum stroke by trial and error adjustment of x. If the stroke is chosen optimally ($x = 1/C_0$), then the maximum sensitivity $S_{max} = e^{-1}/C_0$. From this equation it can be seen that the sensitivity increases as the absorption coefficient decreases and vice versa.

Another method to get a measurement of the absorption coefficient would be to compute a "difference over sum" of the two photodiode currents. This computation may be easier to implement in electronic hardware. The "difference over sum" is defined in equation (7) below as A:

$$A = \frac{I_{X-x} - I_X}{I_{X-x} + I_X} = \frac{1 - e^{-Cx}}{1 + e^{-Cx}} = \text{Tanh}\left(\frac{Cx}{2}\right) \quad (7)$$

Again, it is possible to maximize the sensitivity with respect to concentration variations around a nominal concentration $C_0$ by computing:

$$S = \frac{dA}{dC} = \text{Sech}^2\left(\frac{C_0 x}{2}\right)\frac{x}{2} \quad (8)$$

As above, this sensitivity S is a function of the stroke x. Maximum sensitivity is found when:

$$\frac{dS}{dx} = 0 = 1 - \frac{C_0 x}{2} \text{Tanh}\left(\frac{C_0 x}{2}\right) \quad (9)$$

The solution to this transcendental equation is $C_0 x = 1.54$, which corresponds to a nominal "difference over sum" (A) of 0.65. Again, this provides a good method for adjusting the stroke x.

Figure 2:
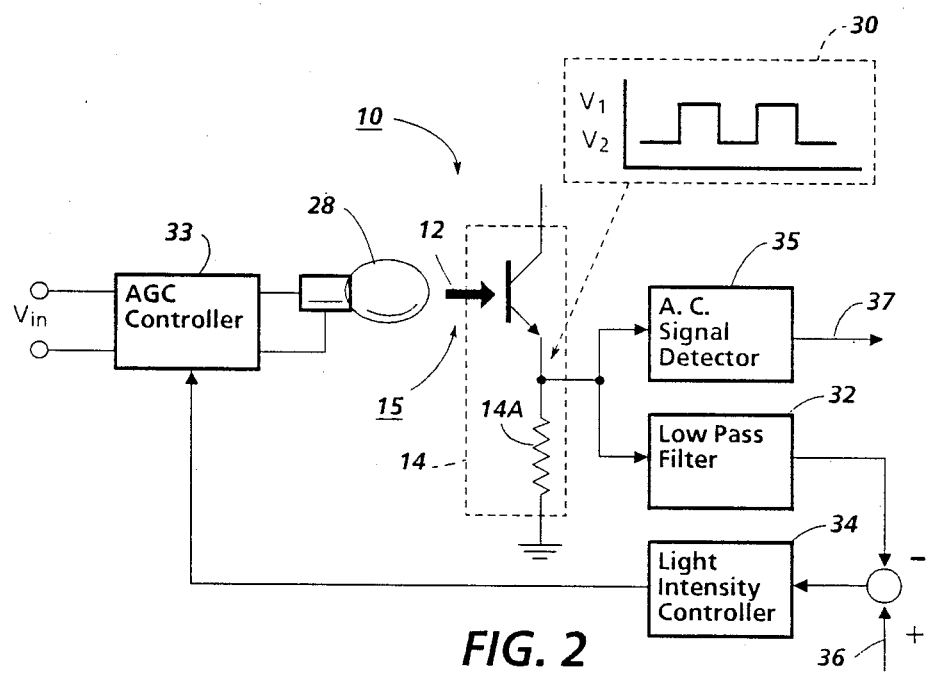
FIG. 2 is a signal processing diagram of the particle concentration measuring device of FIG. 1.

As was mentioned before, the "difference over sum" measurement yields simpler electronic signal processing. If the sum is held constant, then the difference is a function of concentration. One way to accomplish this is illustrated in FIG. 2. A variable intensity incandescent light 28 (e.g., flash light or halogen light bulb) serves as the light source in the particle concentration measuring device 10. The modulation of the channel width 15 results in a square wave voltage signal 30 across the photodiode resistor 14a as shown in the figure within the rectangle in a dashed line. The average value ($V_1+V_2$)/2 of this signal at the output of the low pass filter 32 is proportional to the average light intensity onto the photodiode 14 and also is half the sum in the "difference over sum" measurement. This value is kept constant by a light intensity controller 34 which adjusts the gain in an adjustable gain control (AGC) loop comprising AGC controller 33, photodiode 14, low pass filter 32, light intensity setpoint 36, and light intensity controller 34. Thus, by controlling the voltage to the light bulb 28, its intensity is controlled. Now that the sum is always constant, the difference $V_1 - V_2$ becomes the signal that is a function of concentration as indicated by arrow 37. An a.c. signal detector 35 consists of a rectify and filter circuit (not shown) yields an analog signal 37 that is a function of concentration.

In cases where it is impractical to control the intensity of the light source (e.g. with a laser source), one could control the sensitivity of the photodetector by adjusting the photodiode resistor so as again to keep ($V_1+V_2$)/2 constant. A voltage controlled resistor circuit (not shown) could easily perform this. Note, that this essentially is the same as an AGC circuit.

The above analysis and explanation of operation forms the basis for the particle concentration measuring device of the present invention, specifically designed to measure the concentration of black or colored toner particles in isopar liquid. This concentration is a function of the transmissibility of light through the liquid.

Figure 3:
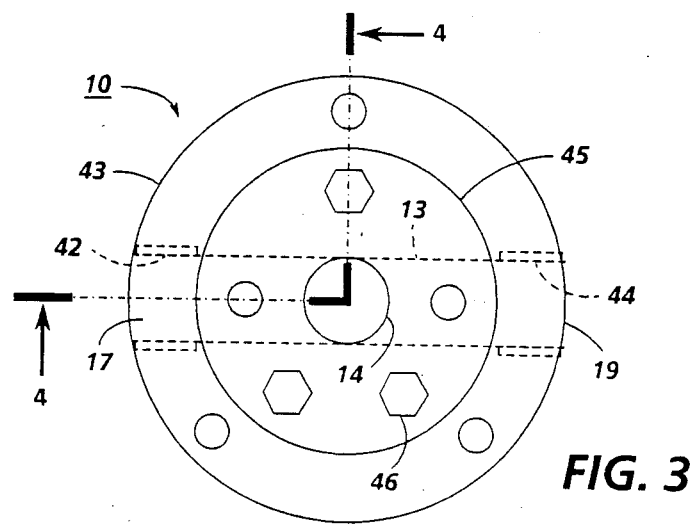
FIG. 3 is a plan view of the particle concentration measuring device of the present invention.
Figure 4:
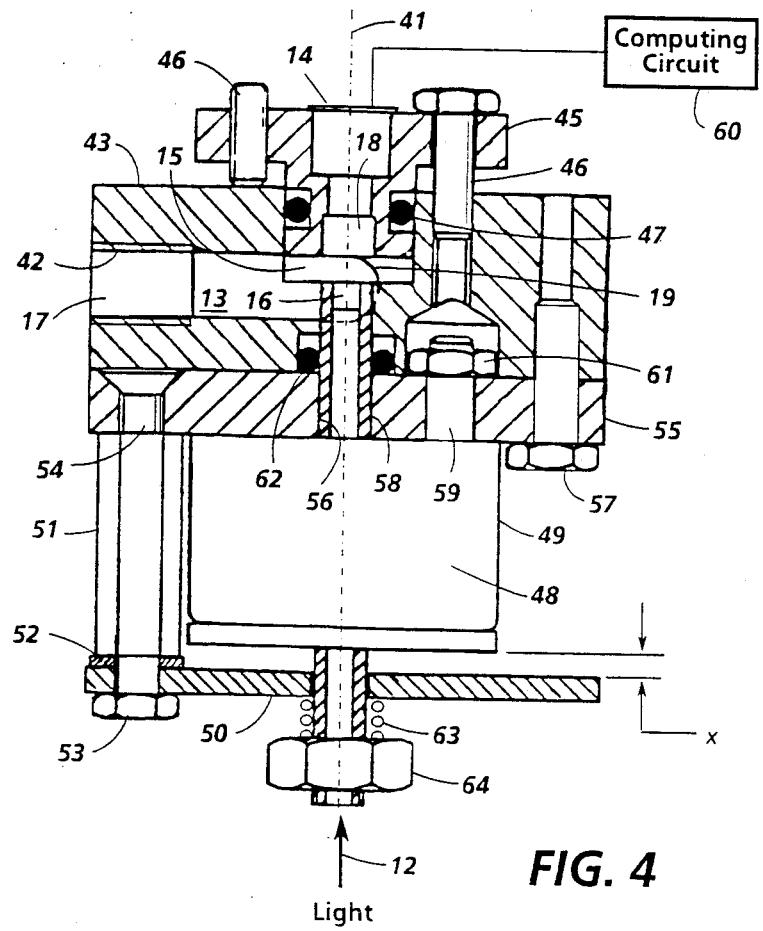
FIG. 4 is a cross-sectional view of FIG. 3 as viewed along section line 4—4.

A preferred embodiment of the particle concentration measuring device 10 is shown in FIGS. 3 and 4. FIG. 3 is a plan view and FIG. 4 is a cross-sectional view taken along view line 4—4 in FIG. 3. Note that the view in FIG. 4 on the right hand side of the center line 41 is rotated 90° with respect to the left hand side as indicated by the view line 4—4. Hence, one can mirror image either side to get the appropriate straight cross-sectional views. Fluid (not shown) is admitted through a fitting (not shown) which screws into tapped entrance hole 42 or entrance 17 in the main body 43 of the measuring device 10. A straight hole 13 through the main body is the fluid channel in which the fluid passes as schematically illustrated in FIG. 1. However, since the left hand view is rotated 90° with respect to the right hand view, the tapped exit hole 44 or exit 19 of the channel is shown as if the fluid is flowing down into the surface of the drawing. A photodetector holder 45 adjustably supports the photodetector or photodiode 14, holds stationary viewing window 18 and any focusing lens 20, if required (not shown in FIG. 4), and provides for adjustment of the nominal channel width through adjustment screws 46. An "O" ring gasket 47 provides a seal against fluid leakage. The movable window 16, which is reciprocably relocated along the light beam path to change the channel width, is moved by solenoid 48. The stroke x of this solenoid is determined by stops, one being the solenoid housing 49 itself, the other one being stop plate 50. Stop plate 50 is also adjustable through springs 51, washers 52, and long bolts 53 which are adjustably fastened into threaded holes 54 in support plate 55. Support plate 55 has a center hole 56 for slidably receiving hollow center shaft 58 and is bolted to the main body 43 by screws 57. The center shaft 58 is the movable part of the solenoid 48. This shaft is bored out so that the light beam 12 can go through the center of the shaft and the pressed-in window 16. The center of the shaft 58, the light beam path, and the center line 41 of the measuring device 10 are coaxial and thus one and the same. Movement of this shaft 58 changes the movable window location and thus changes the channel width 15 between the fixed window and movable window by moving the movable window from one predetermined position to another predetermined position. Another "O" ring seal or gasket 62 provides the sealing against fluid leaking along the movable shaft 58. The transmissibility of light through the fluid is measured by the photodiode current via computing circuitry 60 as explained above. The solenoid 48 is mounted on support plate 55 by bolts or studs 59 and nuts 61. The return stroke x of the solenoid center shaft 58 is accomplished by a spring 63 against an adjustable nut 64 mounted on a threaded end portion of the center shaft.

Figure 5:
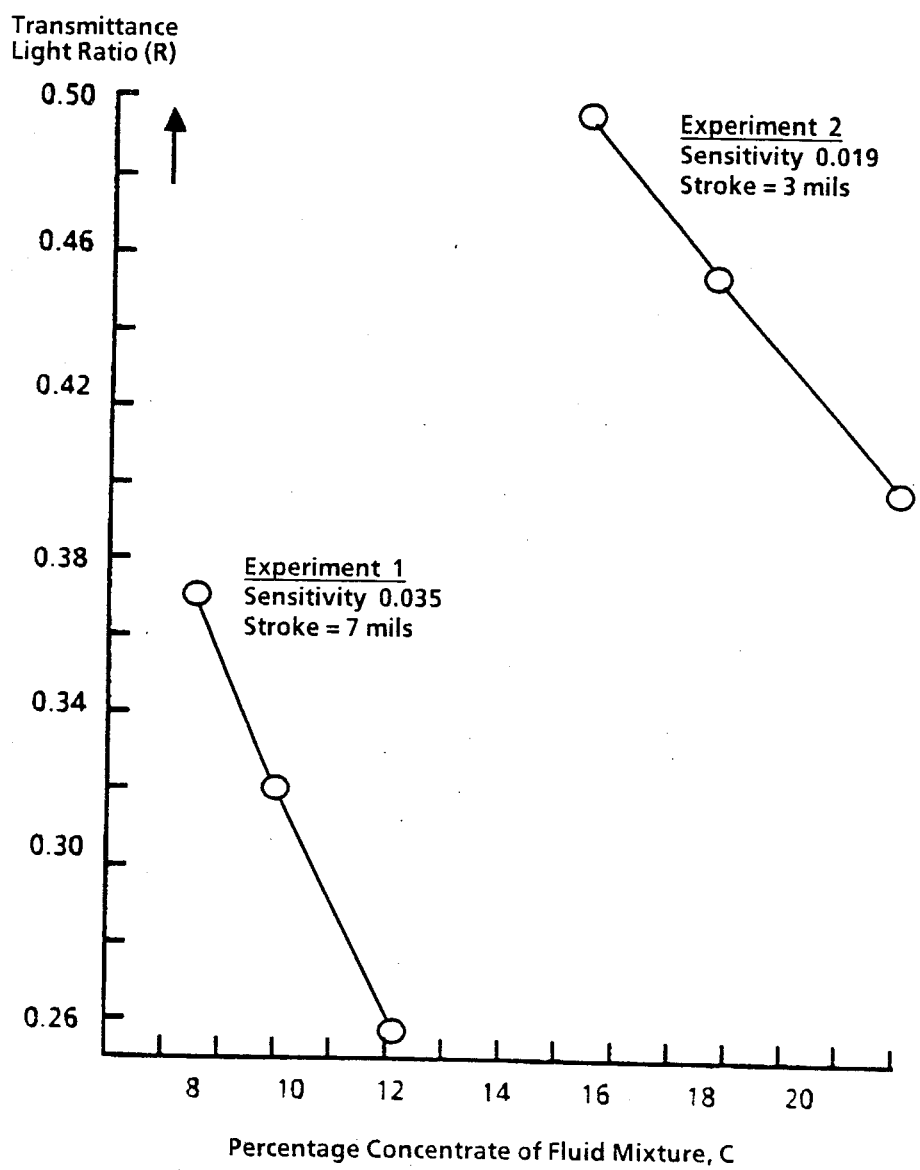
FIG. 5 is a plot of the transmittance light ratio versus percentage of particle concentration in the fluid/concentrate mixture.
Figure 6:
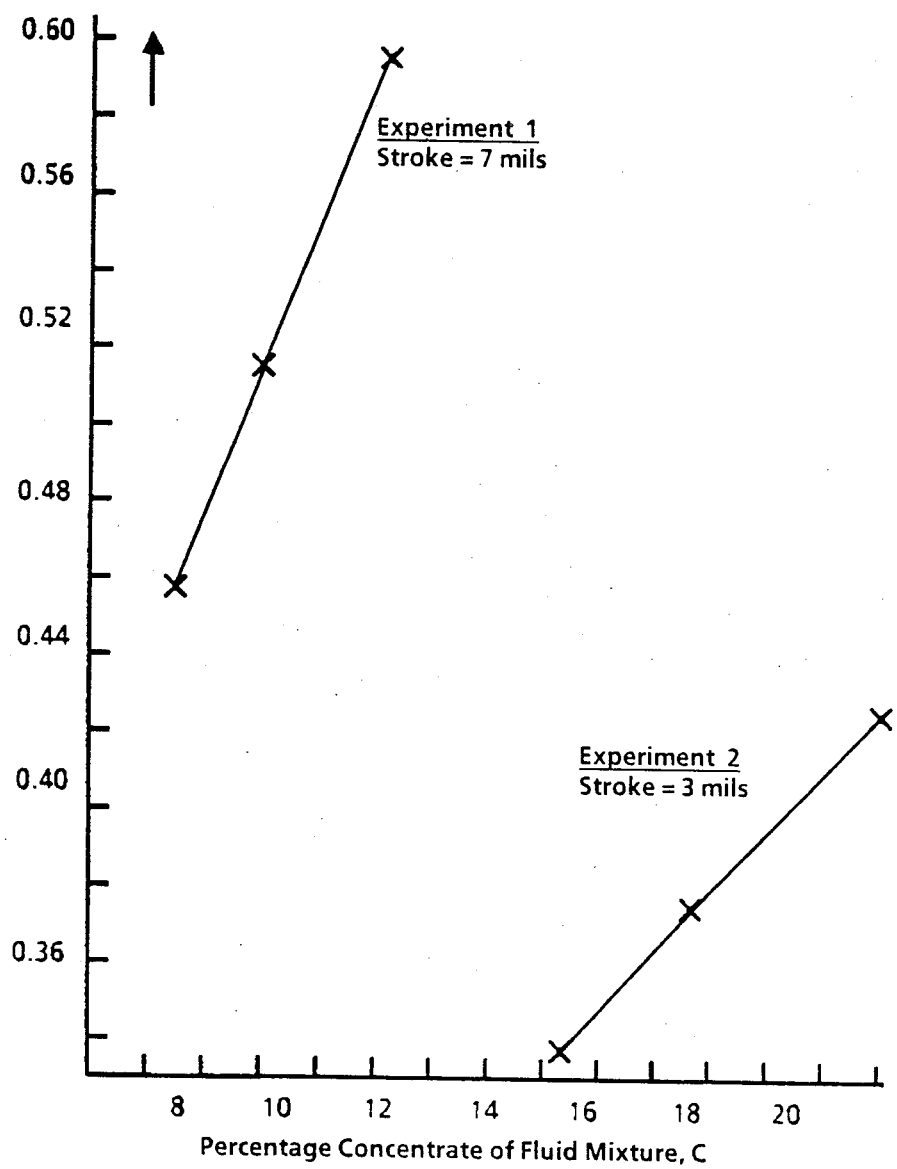
FIG. 6 is a plot of the transmittance light difference over sum versus the percentage of particle concentration in the fluid/concentrate mixture.

A set of experiments was performed to demonstrate the feasibility of the variable path length method of measuring the particle concentration of a fluid. Toner particles or concentrate and isopar were mixed in several different ratios to obtain several fluid concentrations. These fluids were passed through the device in FIGS. 3 and 4 and the photodiode currents at two different channel widths were measured. The ratios "R" were computed and are presented in the plot in FIG. 5. It shows that the ratio R depends almost linearly on the concentration for small changes in this concentration. In the second experiment, the nominal concentration was chosen to be approximately twice that of the first experiment. According to the theory, the sensitivity should then be half. This is confirmed by the data. Also, the stroke x should be decreased to obtain maximum sensitivity which again is confirmed by the data. In experiment 1, three different percentages of toner particles of the toner particle/isopar mixture was used, viz., 8%, 10%, and 12%. A stroke x of 7 mils or 175 $\mu$m was used. In the second experiment, the three percentages of concentrate used was 16%, 20%, and 24% with a solenoid stroke of 3 mils or 75 $\mu$m. For the same experiments, the "difference over sum" was also computed and the results are plotted in FIG. 6. The relationship between "difference over sum" and concentration is quite linear and the proportionality constant changes with the stroke x as is predicted by the theory.

Many modifications and variations are apparent from the foregoing description of the invention and all such modifications and variations are intended to be within the scope of the present invention.

We claim:

1. Apparatus for measuring the particle concentration in a fluid comprising:
   a variable intensity collimated light source;
   means for transmitting a collimated light beam from the light source along a path and through a movable window, the movable window being reciprocally movable along said light beam path;
   a photodetector being spaced from and aligned with the movable window to receive the light beam transmitted from the movable window and to produce an output signal in response thereto;
   means for passing a fluid containing a concentration of particles therein between the movable window and the photodetector;
   means for moving the movable window from one predetermined position to a second predetermined position, so that the output signals from the photodetector are produced in accordance with the two predetermined positions, the two output signals being proportional to the distance of travel of the light beam through the fluid;
   means for controlling the intensity of the light source to maintain the sum of the two different output signals constant, so that the difference in the two output signals is a function of particle concentration; and
   circuit means for computing a difference over sum of the two output signals and determining the particle concentration of the fluid based on the difference over sum computation.

2. The apparatus of claim 1, wherein the light beam path is straight; wherein the fluid containing a concentration of particles is passed between said movable window and a fixed window; wherein the photodetector is spaced adjacent the fixed window; and a focusing lens focuses the light received from the fixed window onto said photodetector.

3. The apparatus of claim 2, wherein the means for transmitting a collimated light beam comprises a translatable hollow shaft open at one end and having said movable window fixedly mounted on the other end, said hollow shaft having seal means to prevent leakage of fluid therepast; and wherein the means for moving the movable window is a solenoid which slidingly translates the hollow shaft through the seal means.

4. The apparatus of claim 3, wherein the means for passing the fluid comprises a housing having a passageway therethrough; wherein the translatable hollow shaft end with the movable window attached thereto penetrates the passageway and confronts a fixed window spaced therefrom which also penetrates the passageway, the movable window and fixed window being aligned to define a variable width throat in the passageway, so that the light beam traveling through the hollow shaft passes through the movable window, fluid, and fixed window before impinging on the photodetector; and wherein the solenoid is fixedly attached to the housing.

5. A method of measuring the particle concentration in a fluid comprising the steps of:
   transmitting a collimated beam of light from a variable intensity light source along a path and through a movable window;
   detecting the light beam with a photodetector spaced from the window and aligned with the light beam path, the photodetector producing an output signal in response to detection of a light beam, the output signals varying according to the distance between the movable window and the photodetector;
   reciprocally adjusting the location of the movable window from one predetermined position along the light beam path to a second predetermined position, so that two different output signals are produced;
   passing a fluid containing a concentration of particles therein between the movable window and the photodetector during the transmittal of light beams;
   controlling the intensity of the light source to maintain the sum of the two different output signals constant, so that the difference in the two output signals is a function of particle concentration; and
   computing a difference over sum of the two different output signals and determining the concentration of the particles in the fluid based on the difference over sum computation.

* * * * *